US00PP26351P3

(12) United States Plant Patent
Schoone

(10) Patent No.: US PP26,351 P3
(45) Date of Patent: Jan. 26, 2016

(54) PHALAENOPSIS ORCHID PLANT NAMED 'JAZZ'

(50) Latin Name: *Phalaenopsis hybrida*
Varietal Denomination: Jazz

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 135 days.

(21) Appl. No.: 13/998,017

(22) Filed: Sep. 24, 2013

(65) Prior Publication Data

US 2014/0090132 P1 Mar. 27, 2014

Related U.S. Application Data

(60) Provisional application No. 61/704,883, filed on Sep. 24, 2012.

(30) Foreign Application Priority Data

Sep. 27, 2012 (NL) ..... PBR OPS966

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Susan McCormick Ewoldt
(74) *Attorney, Agent, or Firm* — Foley & Lardner LLP; Sunit Talapatra

(57) ABSTRACT

A new and distinct *Phalaenopsis* plant named 'Jazz' particularly characterized by flowers which are red/purple with a white mark in the center; labellum is red/purple with white and some yellow; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Jazz'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Jazz'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Jazz' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Jazz' originated from a cross made by the inventor in 2000 in Strengweg, Heemskerk, The Netherlands. The female or seed parent is the *Phalaenopsis* cultivar designated 'Taisuco Firebird', unpatented. The male or pollen parent is the *Phalaenopsis* cultivar designated 'Strawberry', unpatented. The new *Phalaenopsis* 'Jazz' was discovered and selected by the inventor as a single flowering plant within the progeny of the stated cross in a controlled environment in 2008 in Strengweg, Heemskerk, The Netherlands.

Asexual reproduction of the new *Phalaenopsis* cultivar by tissue culture was first performed in July, 2008 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Jazz', which in combination distinguish this *Phalaenopsis* as a new and distinct cultivar:

1. flowers which are red/purple with a white mark in the center; labellum is red/purple with white and some yellow;
2. plant produces more than one inflorescence;
3. plants may be propagated economically and uniformly using tissue culture;
4. inflorescence is long and sturdy; and
5. relatively short, dark-green foliage In comparison with the parental cultivars of 'Jazz', the female parent 'Taisuco Firebird' has dark pink colored flowers with a red/purple labellum and are about 11 cm in size. The male parent 'Strawberry' has pink colored flowers and are about 12 cm in size, whereas the flowers of 'Jazz' are red/purple with white mark in the center and a red/purple labellum. 'Jazz' is about 11 cm in size.

Presently, the commercial cultivar to which 'Jazz' can be meaningfully compared is 'Easter Egg' (Patented, U.S. Plant Pat. No. 24,448). The flowers of 'Jazz' are darker in color than the flowers of 'Easter Egg'. They both have white in the center, only 'Easter Egg' has more white than 'Jazz'. The shape of the labellum differs and 'Jazz' has more and darker purple in the labellum than 'Easter Egg'.

BRIEF DESCRIPTION OF THE PHOTOGRAPHS

The accompanying photographs illustrate the overall appearance of the new *Phalaenopsis* 'Jazz' showing the colors as true as is reasonably possible with colored reproductions of this type. Colors in the photographs may differ slightly from the color values cited in the detailed botanical description, which accurately describe the color of 'Jazz'.

DETAILED BOTANICAL DESCRIPTION

Figure 1:
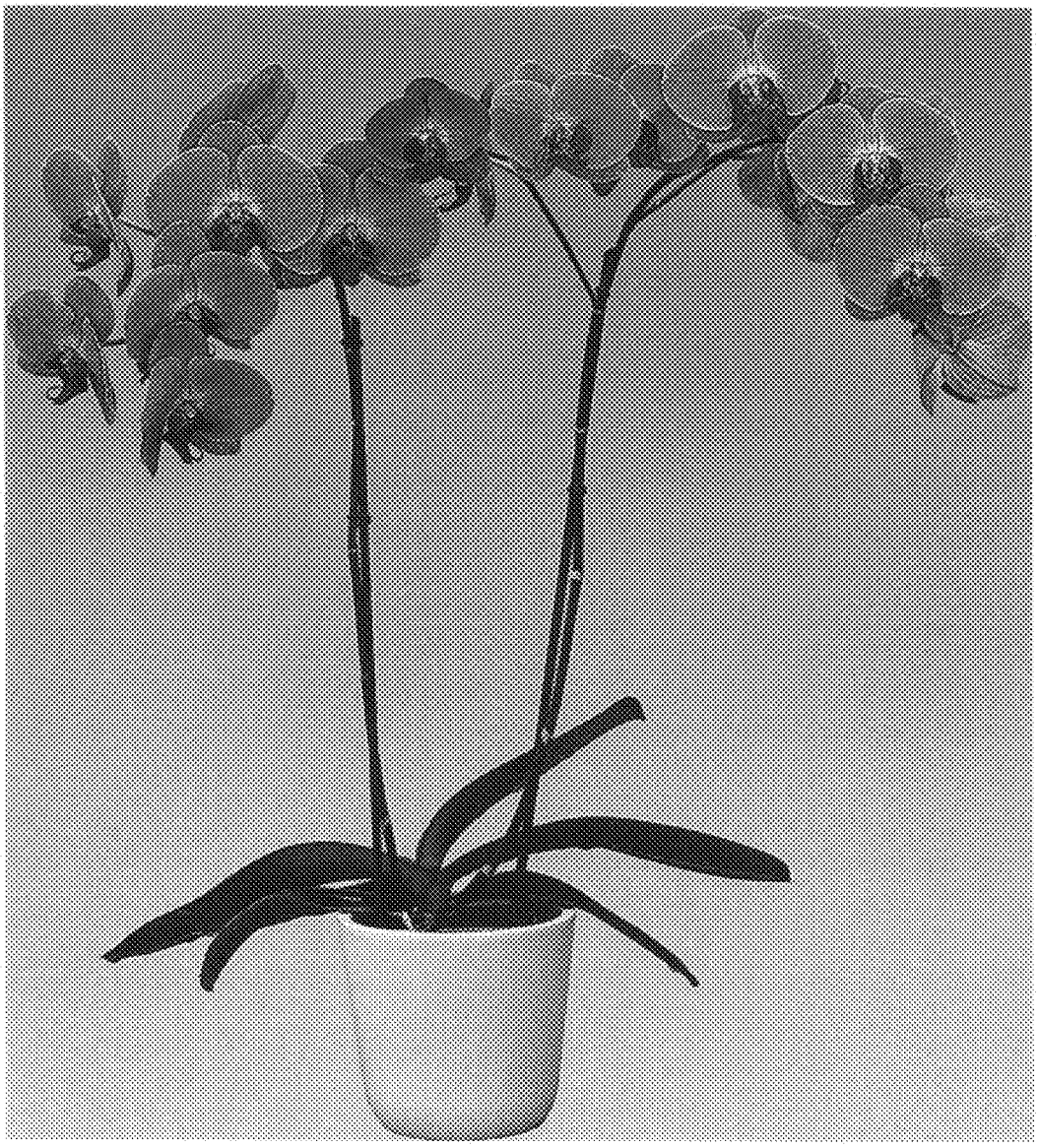
FIG. 1 shows a side view perspective of a typical flowering plant of 'Jazz' in a 12 cm pot, at 16 months of age.

The new *Phalaenopsis* cultivar 'Jazz' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Jazz' as grown in a greenhouse in Strengweg, Heemskerk, The Netherlands, under conditions which closely approximate those generally used in commercial practice. Initially, the ideal temperature to grow plants of 'Jazz' is 27° C. during the day and at night. Then, during the flowering phase of 'Jazz', the ideal growing temperature is 20-22° C. during the day and 18° C. at night. Light levels for growing 'Jazz' are a minimum of 5,000 lux and a maximum of 10,000 lux. A balanced fertilizer with level of 200 ppm N, 87 ppm P, 168 ppm K is applied. Duration of growth of 'Jazz' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Jazz' plants described is 12 months after potting.

Classification:

*Botanical.—Phalaenopsis hybrida.*

Parentage:

*Female or seed parent.—Phalaenopsis* cultivar designated 'Taisuco Firebird', unpatented.

*Male or pollen parent.—Phalaenopsis* cultivar designated 'Strawberry', unpatented.

Propagation:

*Type.*—Tissue culture.

*Rooting habit and description.*—Fleshy; approximately 4 mm-7 mm wide and grey/green in color (RHS 190B); freely branching. It takes 12 weeks for plants growing in tissue culture to initiate roots.

Plant:

*Size at maturity.*—Height (from bottom of pot to highest flower): about 65 cm. Spread: about 55 mm.

*Growth habit.*—Normal; dark green leaves (RHS N137C) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-2 racemes with flowers appear.

Foliage:

*Quantity per plant.*—About 5 to 7 leaves are produced before flowering.

*Arrangement and attachment.*—Half up/horizontal and on two sides.

*Overall shape of leaf.*—Oval and narrow; the tips are asymmetric, some are blunt, some are pointy.

*Texture (upper & underside).*—Smooth and leathery.

*Pubescence.*—None.

*Mature leaf length.*—About 15 to 29 cm.

*Mature leaf width.*—About 6 to 9 cm.

*Mature leaf thickness.*—About 2 mm.

*Mature leaf color (upper surface).*—Green (RHS N137C).

*Mature leaf color (under surface).*—Green (RHS 146A).

*Leaf base.*—Acute.

*Margin.*—Entire.

*Venation.*—Pattern: parallel. Color of midvein: upper surface: green (RHS N137B). under surface: green (RHS 146A).

Inflorescence description:

*Appearance.*—Upright to slightly pendant, racemose inflorescence with bilaterally symmetrical flowers that open in succession beginning with the lowermost flower.

*Raceme.*—Quantity per plant: about 1 to 2. Number of flowers per raceme: about 10 to 18. Length: about 50 to 70 cm.

*Peduncle.*—Diameter: about 4 to 7 mm. Strength: strong. Aspect: upright. Texture: glabrous and smooth. Color: brown (RHS N200A) with green spots (RHS 141C).

*Buds.*—Height (from base to tip): about 23 mm to 30 mm. Diameter (at midpoint): about 17 mm to 24 mm. Shape: oval/egg-shaped. Color: Main color is red/purple (RHS 72A) at the base some green/yellow (RHS 145B) and violet stripes (RHS 86A).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 1-2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
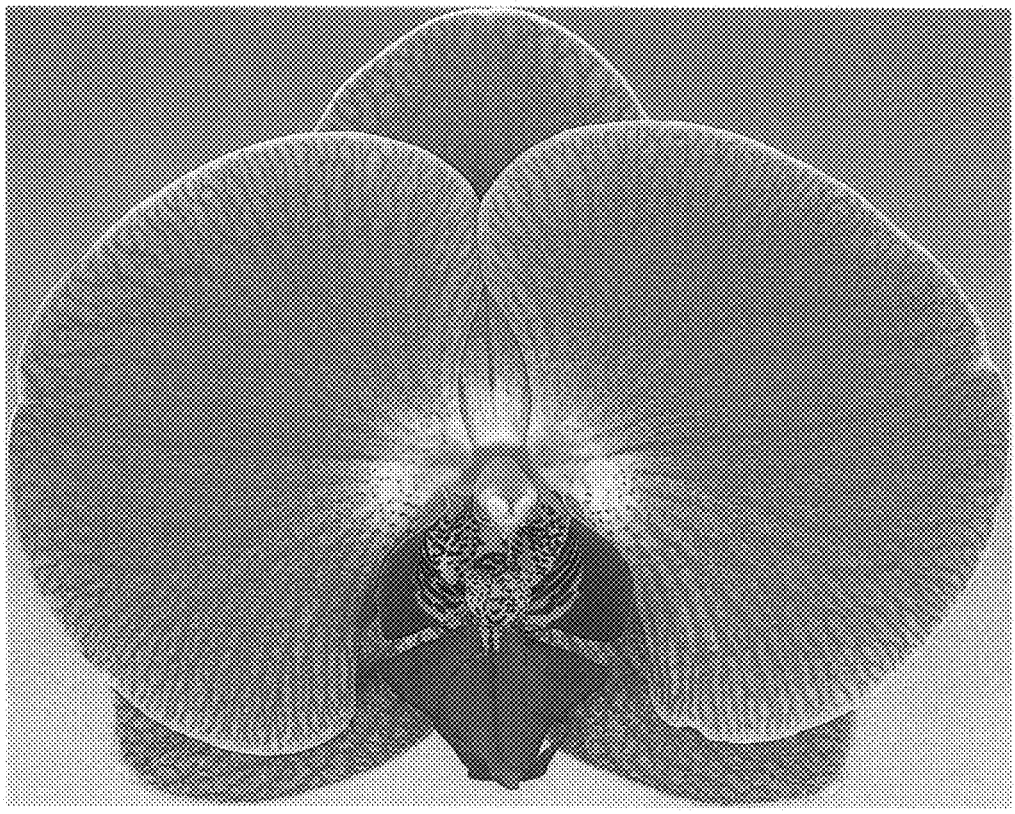
FIG. 2 shows a close-up view of a typical flower of 'Jazz'.
Figure 3:
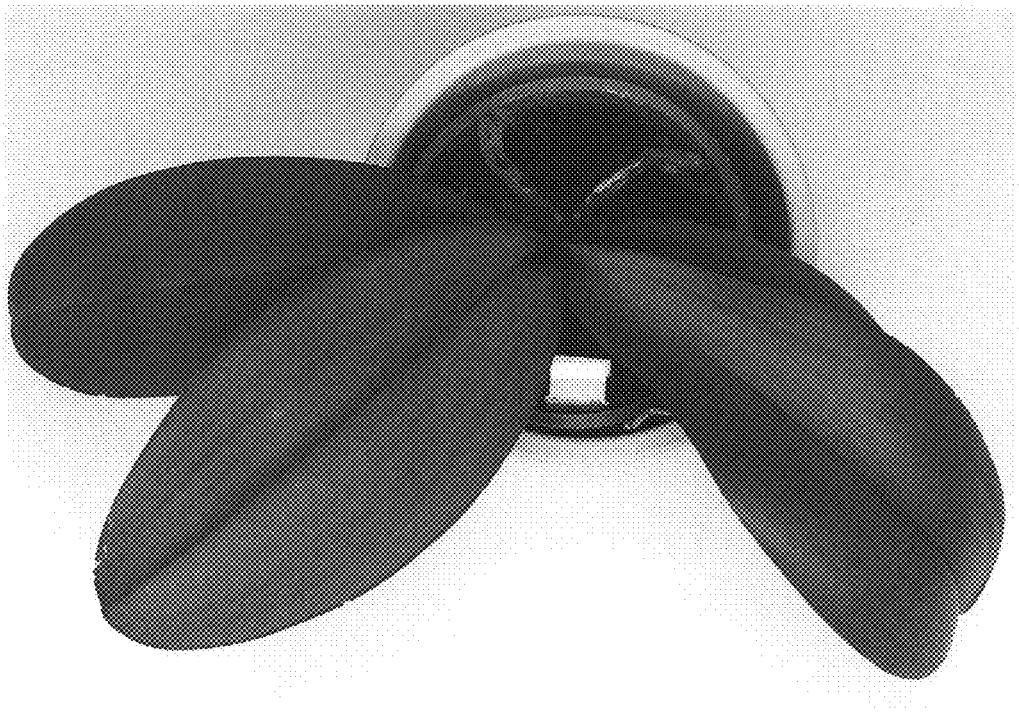
FIG. 3 shows a close-up view of the typical leaves of 'Jazz'.

*Flower*.—Rate of opening: Flowers fully opened about 2 to 3 days after petal and sepal separation. Orientation at opening: slanted upward and outward. Shape: Typical shape of *Phalaenopsis* orchid; see FIG. 2. Size (of single bloom): Height: about 55 mm to 80 mm. Diameter: about 70 mm to 110 mm. Quantity and arrangement: three petals and three sepals that are trimerous, overlapping and arranged in 2 whorls. Petals are more pronounced than sepals. Petals: Arrangement: Inner whorl comprises 3 petals: 2 lateral petals and a labellum. 2 lateral petals: Overall shape: broadly ovate and weakly cupped. Apex: oval with a little notch. Margin: entire and weakly undulate. Base: broadly ovate. Length: about 40 mm to 52 mm. Width: about 30 mm to 40 mm. Texture: Upper surface: smooth and satiny. Under surface: smooth and satiny. Color (when fully opened): upper surface: red/purple (RHS 72B). The veins are purple/violet (RHS N80A). A small purple edge on the outside (RHS 76D), at the base white (RHS NN155C). Under surface: purple (RHS N78C). The veins are red/purple (RHS N74A). At the base some white (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: oval. Length: about 25 mm. Width (not flattened): about 26 mm. Depth of tube created by lateral lobes of labellum: about 17 mm. Texture: Upper & under surface: smooth and satiny. Color (when fully opened): Midlobe: upper surface: red/purple (RHS N78A). At the base in the corners some grey/red (RHS 182C) and at the base in the center a little yellow (RHS 8C). Under surface: purple (RHS N78A). In the center purple (RHS 75A). At the base in the corners a little grey/red (RHS 182C). Lateral lobes: upper surface: red/purple (RHS 72B). At the base white (RHS NN155C) with purple stripes in it (RHS N77C). At the upper edge also some white (RHS NN155C). Under surface: red/purple (RHS 72B). From base till half way on the upper side a wide white edge (RHS NN155C). On the lower edge some grey/purple (RHS 183C). Cirrhi: about 20 mm (long and little curly). Color: red/purple (RHS 72A). Pestle (Callosities): Length: about 5 mm. Width (not flattened): about 7 mm. Color: yellow (RHS 13A) with red/purple spots (RHS 60A).

*Sepals*.—Arrangement: Outer whorl of petals comprises 3 sepals, one dorsal and two lateral sepals. Overall shape: oval and weakly cupped. Length: about 33 to 44 mm. Width: about 24 to 34 mm. Margin: entire and weakly undulate. Apex: oval, lateral more pointed than dorsal. Texture: Upper & under surface: smooth and satiny. Color (when fully opened): Dorsal sepal: upper side: purple (RHS N78A), the veins are red/purple (RHS N81A). At the base white and some white spots all over (RHS NN155C). Also a small edge around the dorsal sepal is white (RHS NN155C). In center at the base some purple/violet (RHS N80D). under side: purple (RHS N78C). the veins are red/purple (RHS N84A). A thin white edge all the way around and some white spots all over (RHS NN155B). Lateral sepals: upper side: purple (RHS N78A). The veins are red/purple (RHS N81A). At the base white spots (RHS NN155C), below green/white (RHS 157A) with red/purple spots (RHS N81A). Under side: purple (RHS N78C). The veins are red/purple (RHS N81A). A thin white edge all around and some white spots all over (RHS NN155B).

*Pedicel*.—Length: about 20 to 40 mm. Diameter: about 4 mm. Texture: glabrous and smooth. Color: at the flower green/white (RHs 157C), then yellow/green (RHS 145B) and then yellow/green (RHS 145A) with a haze of purple/red (RHS 72B).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 10 mm. Diameter: about 6 mm. Color: purple (RHS N78B) and RHS N78A with some white (RHS NN155C).

*Pollinia*.—Quantity: two. Size: about 1 mm. Color: orange (RHS N25A).

*Ovary*.—Length: about 3 mm. Diameter: about 2 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Jazz', as illustrated and described herein.

* * * * *